(12) United States Patent
Alkan et al.

(10) Patent No.: US 10,929,471 B2
(45) Date of Patent: Feb. 23, 2021

(54) SEQUENTIAL PATTERN MINING (71) Applicant: INTERNATIONAL BUSINESS MACHINES CORPORATION, Armonk, NY (US)

(72) Inventors: Oznur Alkan, Clonsilla (IE); Michele Berlingerio, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 315 days.

(21) Appl. No.: 15/698,900

(22) Filed: Sep. 8, 2017

(65) Prior Publication Data
US 2019/0080020 A1 Mar. 14, 2019

(51) Int. Cl.
| | | |
|---|---|---|
| *G06F 17/00* | (2019.01) | |
| *G06F 16/903* | (2019.01) | |
| *G06Q 10/10* | (2012.01) | |
| *G06F 16/951* | (2019.01) | |
| *G16H 50/70* | (2018.01) | |
| *G16H 70/20* | (2018.01) | |

(52) U.S. Cl.
CPC ...... *G06F 16/90335* (2019.01); *G06F 16/951* (2019.01); *G06Q 10/10* (2013.01); *G16H 50/70* (2018.01); *G16H 70/20* (2018.01); *G06F 2216/03* (2013.01)

(58) Field of Classification Search
CPC ............. G06F 16/2246; G06F 11/3604; G06F 16/2465; G06F 16/284; G06F 11/3452
See application file for complete search history.

(56) References Cited

U.S. PATENT DOCUMENTS

| | | | |
|---|---|---|---|
| 5,742,811 A | 4/1998 | Agrawal et al. | |
| 6,473,757 B1 | 10/2002 | Garofalakis et al. | |
| 7,991,577 B2 | 8/2011 | Havener et al. | |
| 9,584,965 B2 | 2/2017 | Good et al. | |
| 2011/0071881 A1* | 3/2011 | Zheng | G06Q 30/0201 705/7.34 |
| 2012/0254128 A1* | 10/2012 | Bath | G06F 16/21 707/689 |

(Continued)

OTHER PUBLICATIONS

Batu, "Nonparametric Approaches for Discovering Triggering Events from Spatio-Temporal Patterns," Middle East Technical University Thesis, Oct. 2014, p. 1-90, Department of Information Systems, Graduate School of Informatics.

(Continued)

*Primary Examiner* — Truong V Vo
(74) *Attorney, Agent, or Firm* — L. Jeffrey Kelly (57) ABSTRACT

A method, computer system, and a computer program product for sequential pattern mining is provided. The present invention may include receiving a data mining parameter. The present invention may also include computing a plurality of frequent sequences without temporal annotations based on the received parameters. The present invention may then include extracting a subsequence with temporal annotations for each frequent sequence based on the computed plurality of frequent sequences. The present invention may further include clustering a plurality of temporal intervals using a time window based on the extracted subsequence. The present invention may also include producing an output based on the cluster of plurality of temporal intervals.

17 Claims, 5 Drawing Sheets

(56) References Cited

U.S. PATENT DOCUMENTS

2014/0279243 A1  9/2014 Kukal et al.
2015/0234997 A1  8/2015 Sarrafzadeh et al.
2016/0354024 A1 12/2016 Keshava et al.
2017/0060962 A1  3/2017 Halim et al.

OTHER PUBLICATIONS

Giannotti et al., "Efficient Mining of Temporally Annotated Sequences," Proceedings of the 2006 SIAM International Conference on Data Mining, 2006, p. 346-357.
Guyet et al., "Extracting Temporal Patterns from Interval-Based Sequences," Proceedings of the Twenty-Second International Joint Conference on Artificial Intelligence, Jul. 16-22, 2011, p. 1306-1311, AAAI Press/IJCAI, Barcelona, Spain.
Hung et al., "Clustering and Aggregating Clues of Trajectories for Mining Trajectory Patterns and Routes," The VLDB Journal, Nov. 20, 2011, 24 Pages, Springer-Verlag.
Mell et al., "The NIST Definition of Cloud Computing," National Institute of Standards and Technology, Sep. 2011, p. 1-3, Special Publication 800-145.
Wang et al., "Opportunity Models for E-commerce Recommendation: Right Product, Right Time," SIGIR'13, Jul. 28-Aug. 1, 2013, p. 303-312, ACM, Dublin, Ireland.
Wikipedia, "Dynamic Time Warping," Wikipedia: the Free Encyclopedia, Last Modified on Jul. 19, 2017, p. 1-6, https://en.wikipedia.org/wiki/Dynamic_time_warping, Accessed on Aug. 7, 2017.
Wu, "Spatio-Temporal Data Mining and Analysis of Precipitation Extremes," The University of Sydney Thesis, Feb. 10, 2008, p. 1-84, SID: 200113854, School of Information Technologies.

\* cited by examiner

SEQUENTIAL PATTERN MINING

BACKGROUND

The present invention relates generally to the field of computing, and more particularly to data mining.

Data mining is a process of extracting data from a large dataset to discover a pattern. Sequential pattern mining is a type of data mining that extracts patterns from a dataset to discover a pattern in a temporal sequence. Data mining patterns with temporal sequential elements may provide insightful information to different industries. Mined data may include telecommunication event logs, processes, medical data, financial data, weather data, traffic data, Internet of Things (IoT) device data, sensor data, and web logs that may be saved on a database. Stored data with time-stamped values may provide both data and a sequence to the data for extracting clear and accurate patterns for mining.

SUMMARY

Embodiments of the present invention disclose a method, computer system, and a computer program product for sequential pattern mining. The present invention may include receiving a data mining parameter. The present invention may also include computing a plurality of frequent sequences without temporal annotations based on the received parameters. The present invention may then include extracting a subsequence with temporal annotations for each frequent sequence based on the computed plurality of frequent sequences. The present invention may further include clustering a plurality of temporal intervals using a time window based on the extracted subsequence. The present invention may also include producing an output based on the cluster of plurality of temporal intervals.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for sequential pattern mining. As such, the present embodiment has the capacity to improve the technical field of sequential pattern mining by identifying sequential patterns with a relative inter-arrival time tolerance. More specifically, a relative inter-arrival time tolerance may mine datasets to produce a sequential pattern output for both uniform temporal distributions and non-uniform temporal distributions. Extracting pertinent information with relative inter-arrival time tolerances from time-stamped subsequence data within a dataset may significantly improve descriptive analytics and prescriptive analytics data mining results by allowing more accurate frequency support for matching subsequences.

As previously described, data mining is a process of extracting data from a large dataset to discover a pattern. Sequential pattern mining is a type of data mining that extracts patterns from a dataset to discover a pattern in a temporal sequence. Data mining patterns with temporal sequential elements may provide insightful information to different industries. Mined data may include telecommunication event logs, processes, medical data, financial data, weather data, traffic data, Internet of Things (IoT) device data, sensor data, and web logs that may be saved on a database. Stored data with time-stamped values may provide both data and a sequence to the data for extracting clear and accurate data patterns.

Large stored datasets of both structured data and unstructured data may unlock insights into relevant patterns that enhance, affect or change industries if the mined data displays an accurate description of data patterns. In order to extract accurate descriptive analytics that may also lead to accurate predictive analytics, the data mining algorithms may play a significant role in sequential pattern outputs. Additionally, with IoT devices quickly expanding the amount of data available, accurate data mining output may assist with decisions by, for example, governments and corporations. Large scale decisions, such as how doctor's treat a patient's symptoms for example, may be assisted by improving the accuracy of pinpointing the best treatment or therapy for patients and may save costs and time by doctor's identifying the cause of particular symptoms faster with large global dataset access. IoT devices, for example, in the medical field, may track patient symptoms and data such as blood pressure or body temperature at any given time if a sensing device is attached to the patient. IoT devices significantly increase the amount of data that may become available for data mining.

Prior to sequential pattern mining, data was extracted as an item or a transaction without sequential information or timestamps of the items. A single transaction, for example, may list the items (i.e., itemset) bought in the single transaction. The nonsequential data may show that an item was purchased or a transaction happened in no particular order. The data was mined, for example, to determine which itemsets were purchased together at a supermarket. If two supermarket customers, customer A and customer B, purchased the same two items $\{X, Y\}$ then the two items $\{X, Y\}$ may have a support frequency of 2 in the mined dataset. A support frequency may represent the frequency in which the item or itemset occurred, for example, each time $\{X, Y\}$ were purchased together. Support and support frequency may refer to how often an itemset matches in a database or in multiple databases (e.g., how many times {X, Y} are purchased together at a supermarket, or at multiple supermarkets).

Then a sequential element to data mining was introduced to determine frequent sequences in sequential data. The order of events and the timing of the events may capture important information for data mining purposes. A sequence may be a list of transactions, elements or events in order of time. Each transaction, element or event may contain an item or an itemset that may produce subsequences within a sequence. For sequential data mining to occur, any stored data may be used for mining purposes if more than one data point exists and the data points have a time-stamp. More than one data point with time stamps create a sequence. The data point may identify what happened (e.g., an event, a transaction, or an appointment) and the data point may identify when the event, transaction or appointment happened. Identifying data points in a temporal order may provide a basis for sequential pattern mining.

Data may be mined for sequences or subsequences in order of the time-stamped input data stored in a database. Sorting the data by the time the event or transaction occurred provides a sequence of data and the details of each event or transaction may provide subsequences of data. A subsequence may be extracted from a sequence and a minimum support of a subsequence is the number of times the subsequence of itemsets match. Minimum support may be specified by the user in a sequential pattern mining program as a minimum number of times a subsequence appears in a dataset for the subsequence to be useful to the user. A subsequence may include, for example, specific time-stamped items contained in an original sequence. For example, a sequence of supermarket transactions contains many itemsets of groceries that were purchased by consumers. The sequence is the list of consumer transactions and each transaction contains a list of specific items that were purchased at the same time. A consumer transactional example may include customer A going to the supermarket every week and the weekly supermarket visit may be considered a sequence or a frequent sequence. Customer A purchases itemset {X, Y} in each transaction each week. {X, Y} may be considered frequent subsequences of customer A's weekly transactions in the supermarket's stored data.

Mining data for a sequential subsequence may remove the transaction element and contain, for example, a list of all groceries purchased within a timeframe from consumers. Mining data for subsequent patterns that match in product and time may not require mining the sequence of transactions, rather just mining the subsequences of specific purchases with time stamps. An example in the medical field may include patient's data entered into the hospital database for each doctor visit. The visit may be the event and the data entered in the event is the subsequence of data. Each visit (i.e., event), the doctor may log the patient's weight, blood pressure, vision test results and blood test results (i.e., an itemset of data or a subsequence of data). Additional patient visits may form a more robust sequence of data, which will expand the subsequence of data. IoT sensing devices in the medical field may also expand the amount of sequential data available in mining databases.

If attempting to find a pattern of blood pressure at particular weights, the subsequences of patients' blood pressure when the patient weighed a certain amount may be mined. Another subsequence of various blood test results may be mined, such as white blood cell count, red blood cell count and cholesterol count. The subsequence of data may have a time-stamp dated the same date and time as the sequence of each patient's doctor's office visit or the time the IoT medical sensing device provided data. The limiting factor of mining data in this example is that only data matches (i.e., support or support frequency) for data matching the transactions from the same day, or transactions that occurred at the same time, may be provided without a time tolerance variance. Insightful data may be missed without the ability to vary the time tolerance, such as, two different patients' blood test results align with the same red blood cell count, however, the blood tests were not taken in a time alignment and the data mining output results may be missed by conventional data mining algorithms (i.e., a significant pattern may not be found) unless a time tolerance was used.

Next, recurring sequential data may have a time-stamp associated with the data to mine for sequences that may be either regular or non-regular sequences. A regular sequence may include a weekly pattern for a particular event (i.e., transaction). A non-regular sequence may include a pattern such as an event occurred today, then in 1 week, then in 1 week and 2 days, and then in 3 weeks. Recurring sequential data mining may determine frequent sequences of events or subsequences with frequent time intervals between each sequence or subsequence where the time intervals may be regular or irregular. For example, customer A goes to the supermarket every week and customer B goes today, then in 1 week, then in 1 week and 1 day. Mining recurring sequential data with a time stamp associated with the data may show that among all the supermarket customers, {X, Y} are typically purchased together once per week or more often if the customer base for the supermarket is large, however, the data mining algorithm may not produce results if {X, Y} are not purchased every recurring 7 days (i.e., week).

Then, a fixed inter-arrival time tolerance was added to sequential pattern mining. A fixed inter-arrival time tolerance for sequential pattern mining may produce sequences or subsequences that have the same support frequency quantified by fixed time parameters. For example, a fixed inter-arrival time tolerance with a threshold of 1 day would produce mining results with a 1 day variance of sequences or subsequences of data. For example, customer A purchases {X, Y} on day 1 and then on day 365. Customer B purchases {X, Y} on day 2 and then on day 372. A fixed inter-arrival tolerance sequential pattern mining algorithm may not identify items {X, Y} as support for customer A and customer B for days 372 and 365 since the difference between customer A's purchase of {X, Y} and customer B's purchase of {X, Y} was more than 1 day apart. This example may yield a support of 1 for customer A's purchase on day 1 and customer B's same purchase on day 2 since the fixed support threshold is 1 day.

In order for two subsequences to have the same support without a time tolerance, customer A and customer B may both purchase {X, Y}, this time customer A is purchasing {X, Y} today and in 1 week (i.e., day 1 and day 8) and customer B is purchasing {X, Y} today and in 1 week (i.e., day 1 and day 8). The day 1 and day 8 purchases of the same items by customer A and customer B may provide a support frequency of 2. If customer A purchases {X, Y} today and in 1 week (i.e., day 1 and day 8) and customer B purchases {X, Y} today and in 1 week and 5 hours (i.e., day 1 and day 8 plus 5 hours), current applications may treat the two purchases as a different sequence with a support frequency of 1. Adding 5 hours to a 1 week time period is not a substantial amount of time, therefore, the 5 hour differential may provide a benefit to sequential pattern mining if the two sequences were treated as identical sequences. If the customer base was expanded to 1,000,000 customers, a time tolerant support frequency may provide pertinent and insightful data for customers who purchased {X, Y} today and in 1 week +/−5 hours (i.e., day 1 and day 8 +/−5 hours).

If a fixed time tolerance of 1 day is used for a sequential pattern mining algorithm, the 1 day fixed time tolerance is a larger difference out of 1 week than the 5 hour difference proposed in the previous example. If the sequence had been 1 day and 5 hours, then 5 hours out of 1 day is a larger difference than 5 hours out of 1 week. Some mining applications may consider 5 hours out of 1 day to be enough time to consider the sequences as separate sequences. Alternatively, if a fixed time tolerance of 5 hours is used for a sequential pattern mining algorithm, the 5 hours out of 1 day would be a much larger difference than 5 hours out of 1 week, and the 5 hours out of 1 day would be an even larger difference out of 1 month.

A fixed inter-arrival time tolerance may not identify an insightful pattern from the dataset being mined since a 1 day fixed inter-arrival time tolerance is a large amount of time between 1 and 2 days, however, a 1 day fixed inter-arrival time tolerance is a much smaller amount of time out of 365 days. Correspondingly, the 5 hour difference in the previous example is a large amount of time variance out of 1 day compared to a small amount of time variance out of 1 week. The ability to mine for sequential patterns with a corresponding amount of time variance notwithstanding, for example, 1 day, 1 week, 1 month sequences may produce more accurate results where sequences may or may not be treated as the same sequence in data mining. Therefore, it may be advantageous to, among other things, produce a sequential pattern mining system to identify insightful sequential patterns that are not identified with a fixed inter-arrival tolerance by using a relative inter-arrival time tolerance algorithm.

According to at least one embodiment, mining sequential patterns with relative inter-arrival time tolerances may produce more accurate results (i.e., results that may show important patterns that may not be shown with a fixed inter-arrival time tolerance). Mined data using relative inter-arrival time tolerances may provide more accuracy for descriptive analytics to show what is correctly happening within the dataset. Predictive analytics may benefit from more accurate data mining of descriptive analytics. Descriptive analytics may view past performance to understand historical data for mining purposes. Predictive analytics may foresee possible future events based on the descriptive analytics.

Sequential pattern mining may first find a sequence in a database that contains time-stamped individual events. For example, medical records of a patient may show the patient being on a particular medication. Additionally, the patient has blood tests shown in the medical records as being taken today, in 1 week and in 2 weeks. Every time the blood test is taken, values for different variables are obtained, such as red blood cell count, white blood cell count, platelets, hemoglobin, calcium or blood glucose. Each blood test date may be time-stamped and the multiple collected test results may be entered in the medical records for the patient and may provide sequences of items and itemsets.

Sequential pattern mining may discover related patterns in a sequence that may refer to subsequences of items or itemsets in a timestamped database. An item may include one item or value and an itemset may include multiple items with multiple subsequent variables. Both an item and an itemset may have a timestamp associated with each value (i.e., data point). A sequence may include a list of events or transactions in order of the time the event or transaction occurred (i.e., the time the structured or unstructured data was logged into a database or the time a sensor device, such as an IoT device, logged the structured or unstructured data into a database).

The present embodiment of the sequential pattern mining program identifies patterns with a relative inter-arrival time tolerance, for example, when a particular output would provide a support of 2 for a relative inter-arrival time tolerance and a support of 1 for a fixed-inter-arrival time tolerance. Referring to the previous example, customer A purchased {X, Y} on day 1 and day 365 and customer B purchased {X, Y} on day 1 and day 372. The relative inter-arrival time tolerance may be 2% and provide a support of 2 since 1 week out of 365 days is within a 2% temporal window. The fixed inter-arrival time tolerance of 1 day would provide a support of 1 for the same data mining output.

Sequential pattern mining algorithms may produce two distinct patterns. The patterns may have two different sequences using a fixed inter-arrival time tolerance of 1 day and a resulting support of 1. The two produced patterns are A-[1 day]→B-[365 days]→C; and
A-[1 day]→B-[372 days]→C.

The current embodiment may mine the same database using a relative inter-arrival time tolerance such that the above output may be condensed to A-[1 day]→B-[365-372 days]→C, which produces a support of 2, since 7 days out of 365 days is within the relative tolerance of 2%. A fixed inter-arrival time tolerance compared to a relative inter-arrival time tolerance may produce a different data mining output from the same dataset. A relative time-gap tolerance between frequent subsequences (i.e., frequent itemsets) may produce more insightful and accurate data pattern outputs. The present embodiment of the sequential pattern mining program may extract relative time tolerance intervals of data, apply a frequent sequence mining and return (i.e., output) the frequent subsequences within relative time tolerant intervals.

Using a medical industry example, IoT devices may be used to sense medical data remotely. The medical data received may exhibit a high standard deviation of inter-arrival times where intervals may increase over time. For instance, one patient's symptom may appear today or tomorrow, then in 1 month, or in 1 month and 1 week. In this situation, mining patterns with a relative time-stamp tolerance between subsequent events may produce the results associated with a particular symptom even though the results were not collected on a consistent basis, such as every week from a doctor's appointment. For example, a patient has a blood test taken every week and then develops symptoms. Then a check may be done (i.e., data may be mined) for symptoms and blood tests every week. The patient, however, may miss the weekly blood test deadline and instead has a blood test taken one day earlier or later than the one week deadline (i.e., +/−1 day variance). Some therapies may have different, non-regular, time intervals for searching for symptoms or for blood tests, such as 1 week, 4 weeks, 3 months, 6 months, and 12 months. The one day tolerance for the weekly blood tests may be a larger time tolerance than missing a weekly interval (i.e., deadline) compared to the one day tolerance of the test taken of the 1 year deadline (i.e., $1/7^{th}$ of the time tolerance for one day out of one week compared to $1/365^{th}$).

The sequential pattern mining program uses a relative inter-arrival time tolerance to provide a more accurate and relevant output of mined data using a time varying tolerance. Instead of a +/−1 day fixed time tolerance, the sequential pattern mining program may provide an alternative data output based on a varying time tolerance, such as +/−5% or +/−10%. For the non-regular time interval data (e.g., 1 week, 2 months and 12 months) example, using a +/−10% relative inter-arrival time tolerance, the first deadline would be 1 week +/−10% (i.e., 1 week +/− approximately 1 day), the 2 month deadline would be 2 months +/− approximately 9 days and the 1 year deadline would be 1 year +/− approximately 1 month.

Minimum support may be the parameter to show how frequent the data results are provided. A second parameter may be the relative inter-arrival time tolerance percentage. Adjusting the parameters, minimum support and relative inter-arrival time tolerance, may produce different outputs for the same dataset. Analysis of stored data may be used for different purposes. For example, a 2% relative inter-arrival time tolerance may produce a different data output than setting the relative inter-arrival time tolerance to 5%. Also, altering minimum support values may produce a different data output.

If multiple events with subsequences are logged by many patients, for example patient tests (e.g., blood test) administered at doctor visits or from IoT sensor devices logging a patient's heart rate and blood pressure, the dataset may be expanded to provide a larger output of data to be identified as relevant to a particular patient's symptoms or blood test results. For example, three patients', P1, P2 and P3, blood tests are taken where the sequences are aligned to find a common pattern. P1 and P2 test results are negative for test T. The data mining output using the sequential pattern mining program may produce patterns of frequent subsequences between T. The aligned test results in sequential pattern mining may be called minimum support and here, out of 3 blood tests results for test T, 2 test results are a match for being negative for test T, creating a minimum support of 2. If the number of patients were expanded to 1,000,000, then the user may adjust the minimum support parameters and the relative inter-arrival time tolerance parameters to mine for useful sequential patterns. Minimum support is the minimum frequency of the pattern in order to identify the pattern as frequent. A net effect of 1 sequence may yield a minimum support of every subsequence as 1, since there is only 1 sequence present. If there are 10 sequences and all sequences with a minimum support of 1 are mined, then the results may provide a minimum support of 10%. If a minimum support of 10 was mined, then the subsequences may be found in the possible sequences.

Another medical domain example may relate to certain therapies or analyses that may require regular check-ups, however, the timing of the doctor visits may not be in a uniform temporal distribution. For example, photopheresis therapy (i.e., a blood treatment therapy) may be recommended by a doctor after a patient has a kidney transplant and the therapy is applied and clinically assessed on or around the following interval, 1 week, 2 weeks, 1 month, 3 months, 6 months and 12 months. Each patient for a photopheresis therapy may produce a sequence form of A-[1 w]→B-[2 w]→C-[1 m]→D-[3 m]→E-[6 m]→F-[12 m]→G where each letter corresponds to a set of clinical values of the same variables, such as cholesterol levels and iron levels. The data corresponding to the photopheresis therapy for each kidney transplant patient may not be collected on the exact specific day (i.e., 1 week, 2 weeks, 1 month, 3 months, 6 months, 12 months), however, may be collected with slight time delays. The tolerance for each sample collected for the photopheresis therapy may be valid depending on the relative time passed between analyses or relative to the time passed since the last analysis. For example, a doctor may allow sample B to be taken 1 week and 1 day after A, however, may not allow sample B to be taken after 2 weeks. Correspondingly, sample G may be taken after 12 months and 1 week after F. Here, the relative temporal threshold of 2% is shown as F-[12 m+/−2%]→G; or
F-[12 m+/−1 week]→G.

A sequential pattern mining with a fixed inter-arrival time tolerance algorithm may produce different results than the current embodiment of sequential pattern mining with a relative inter-arrival time tolerance. The applicability of sequential pattern mining using a relative inter-arrival time tolerance versus a fixed inter-arrival time tolerance may have an impact on the types of patterns that may enhance many different industries, such as the medical industry, financial industry, and the IoT industry. Sensors may accumulate large datasets and current databases may have allocated years of pertinent mining data. The large amount of accumulated data may be utilized for more accurate data mining patterns using a relative inter-arrival time tolerance.

When mining or extracting frequent subsets of data from a large dataset, an underlying assumption may be something is frequently happening in the dataset and the dataset may contain data that is pertinent to a particular type of data mining, such as medical records mined by a doctor for the benefit of a patient displaying symptoms. The present embodiment may mine data to show what is correctly happening in the data (i.e., descriptive analytics). An alternate embodiment may assist with future predictions (i.e., predictive analytics). Another embodiment may include making recommendations, for example, if customers who typically purchase X then later purchase Y, then a recommendation for product Y may be created for a customer who just purchased X, since customers have been known to purchase both items.

A descriptive analytics example that may create a predictive analysis in the medical domain may consist of amphetamine tested on 1,000 people, and the user may want to know if amphetamine works in at least 95% of the test cases by mining a medical data repository dataset for frequent subsequences within the dataset relating to amphetamine alleviating symptoms. The frequent pattern of observed data and the collection of the most frequent patterns are a description of the dataset. Another descriptive analytics example may include monitoring a patient who is undergoing a particular therapy and tests that may involve frequent doctor visits and frequent blood tests. The sequence, however, for the therapy and tests may be irregular visits, such as 1 week, 1 month, 3 months, 6 months and 12 months. If 1,000 patients in the medical data repository underwent the particular therapy and tests and the user (e.g., doctor) mines for frequent patterns to analyze patient reactions to the therapy and tests, then the user may find a frequent pattern, such as 90% of the patients that weigh more than 90 kilos had a high white blood cell count within 6 months of the therapy. The doctor may use the mined data to predict that patients that weigh over 90 kilos who undergo the therapy and tests risk having a higher white blood cell count in 6 months.

Figure 1:
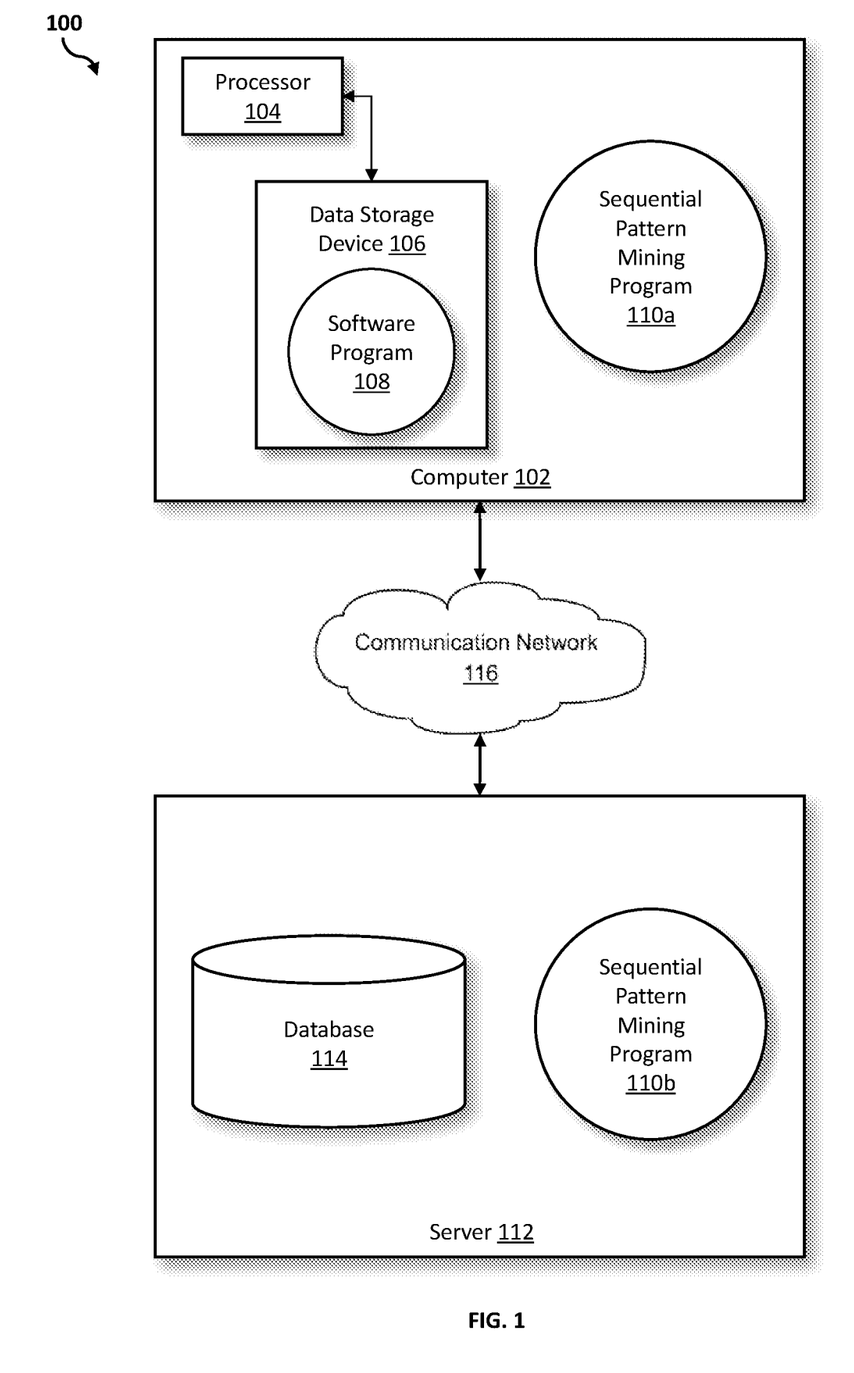
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a sequential pattern mining program 110a. The networked computer environment 100 may also include a server 112 that is enabled to run a sequential pattern mining program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the sequential pattern mining program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the sequential pattern mining program 110a, 110b (respectively) to mine a dataset for relevant sequential patterns. The sequential pattern mining method is explained in more detail below with respect to FIG. 2.

Figure 2:
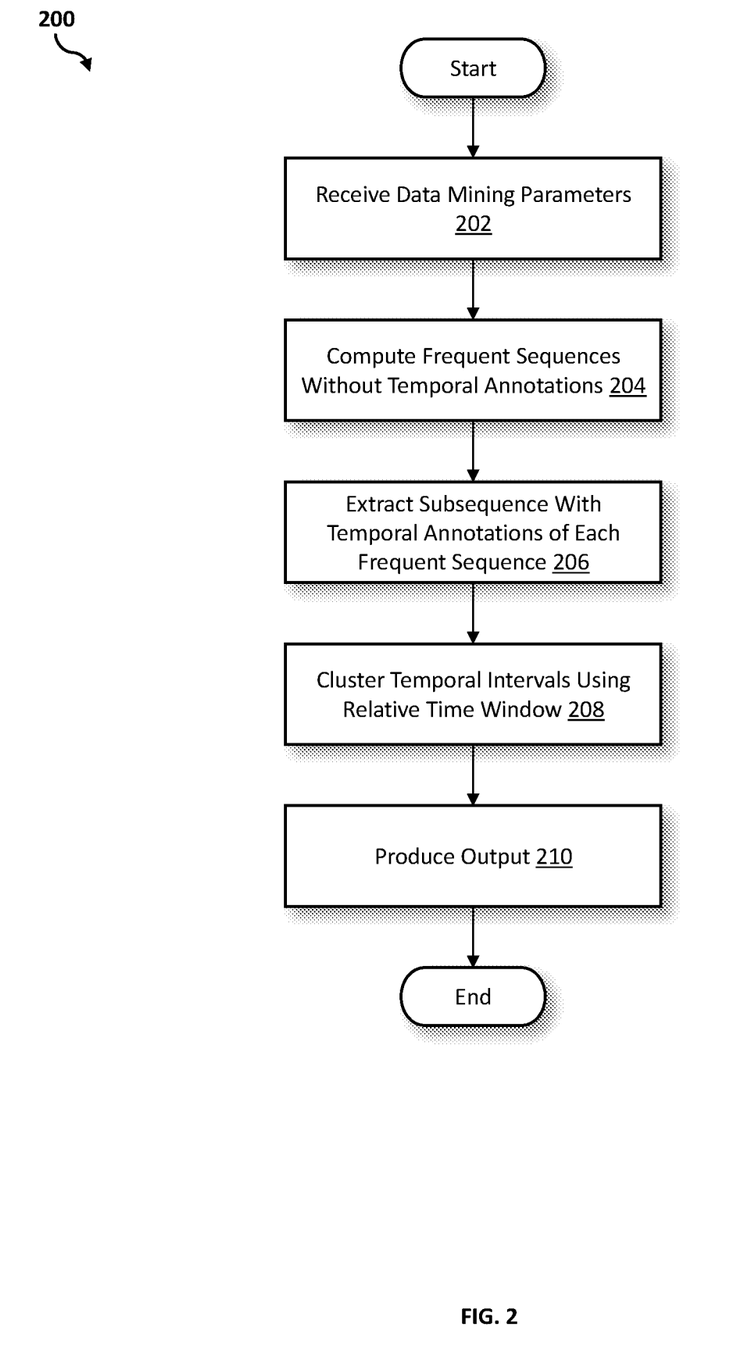
FIG. 2 is an operational flowchart illustrating a process for sequential pattern mining according to at least one embodiment.

Referring now to FIG. 2, an operational flowchart illustrating the exemplary sequential pattern mining process 200 used by the sequential pattern mining program 110a, 110b according to at least one embodiment is depicted.

At 202, data mining parameters are received. The sequential pattern mining program 110a, 110b receives data mining parameters from a user. One data mining parameter the user may enter is a relative inter-arrival time tolerance value, such as +/−5%. The relative inter-arrival time tolerance value may be used to create a relative time window the user sets as a parameter to mine data out of a dataset of sequences and subsequences. The user may set the parameter based on the data being mined. One other mining parameter the user may enter is a minimum support value. The minimum support value may include the number of times subsequences match within the dataset. The user may require more or less matches depending on the data being mined. The minimum support value may be specified by the user into the sequential pattern mining program 110a, 110b as a minimum number of times a subsequence appears in a dataset for the subsequence to be useful to the user.

Once the parameters are received, the sequential pattern mining program 110a, 110b may search datasets in databases (e.g., database 114) and storage media. A dataset may be stored on a computing storage medium, on multiple storage media, on a database storage device or on multiple database 114 storage devices. Datasets may be data existing in a database 114 for different purposes, however, access to the data for data mining purposes may unlock patterns that were not otherwise available. For example, data mined from a database 114 that contains medical data may provide a clear picture to a doctor of matched symptoms from many patients that may help diagnose the doctor's current patient. The database 114 or multiple databases may provide information from global networks (e.g., doctors from many nations) for comparison of symptoms. Data may be accessed by a communication network 116. The communication network 116 may be, for example, a wireless network, a non-wireless network, a secure network or an encrypted network.

Then at 204, frequent sequences without temporal annotations are computed. The sequential pattern mining program 110a, 110b may apply a standard sequential pattern mining algorithm to data in a database (e.g., database 114) that may not include temporal notations. For example, Apriori-based algorithms, projection-based algorithms (e.g., FreeSpan), or sequential pattern discovery using equivalence class (SPADE-based algorithms).

Next at 206, subsequences with temporal annotations of each frequent sequence are extracted. The sequential pattern mining program 110a, 110b may find the temporal intervals for each A→B subsequence based on the sequences mined in step 204. The computed frequent sequences for each A→B sequence may provide the temporal intervals in the data for A→B. The temporal subsequence intervals may be extracted from the sequence of events. For example, a patient's doctor visit may produce a sequence of events. The data collected from the patient's visit to the doctor's office may provide subsequences, such as date and time of the visit, tests completed, test results obtained, symptoms the doctor noted and other general data obtained such as weight and blood pressure taken from a nurse. A collection of events (e.g., multiple patients visiting multiple doctors) may have a time-stamp on the itemset data (e.g., data collected from multiple patients) to form temporal sequences of events and temporal subsequences of itemsets.

At 208, temporal intervals of subsequences using a relative time window are clustered. A density-based algorithm (e.g., DBSCAN) may be used to cluster the extracted subsequences with temporal intervals, however, a relative time-window may also be used with a density-based algorithm. Instead of checking |Ta−Tb|<ft, where Ta is the time-stamp of subsequence a, Tb is the time-stamp of subsequence b and ft is a fixed time tolerance (e.g., 1 day), the sequential pattern mining program 110a, 110b may check if |Ta−Tb|<b*rt, where b is the time that b happened and rt is the relative time tolerance (e.g., 0.3). The relative temporal threshold and a minimum support value may be created by the user and recipient at step 202.

Clustering algorithms may gather data into similar clusters and the density-based algorithm may be one possible method of calculating the cluster of data. The clustering of temporal intervals using a relative time window may be calculated after the density-based algorithm. Instead of checking whether the absolute difference between time-stamp a and time-stamp b may be less than a given threshold, the sequential pattern mining program 110a, 110b may check whether the difference between Ta and Tb is less than the provided relative time tolerance threshold plus a time multiplier. Correspondingly, rather than calculating Ta and Tb not being separated by more than a fixed time tolerance of 1 day, the sequential pattern mining program 110a, 110b may calculate rt*b (e.g., 10% multiplied by the time b happened).

Then at 210, an output is produced. The previously calculated clusters may provide the output data of the relative time tolerance constraint on all of the frequent subsequences gathered. The output may be produced for the user on a computer 102, a server 112 or a computing device where the device may present the data, for example, on a computer monitor or a printed document. The output may be, for example, in the form of a graph, a chart or a list of events on a word processing application.

It may be appreciated that FIG. 2 provides only an illustration of one embodiment and does not imply any limitations with regard to how different embodiments may be implemented. Many modifications to the depicted embodiment(s) may be made based on design and implementation requirements.

Figure 3:
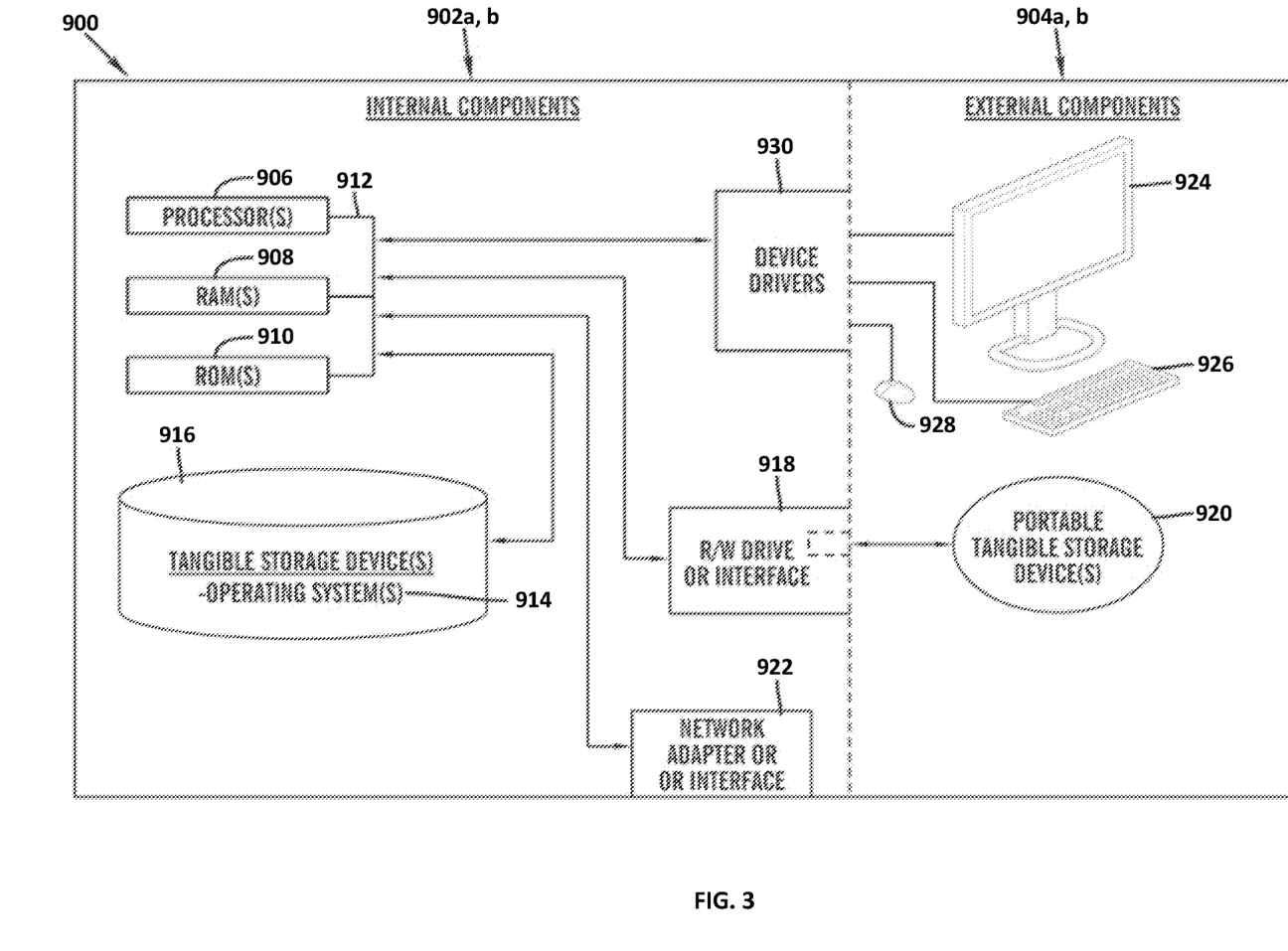
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908, and one or more computer-readable ROMs 910 on one or more buses 912, and one or more operating systems 914 and one or more computer-readable tangible storage devices 916. The one or more operating systems 914, the software program 108 and the sequential pattern mining program 110a in client computer 102, and the sequential pattern mining program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the sequential pattern mining program 110a, 110b can be stored on one or more of the respective portable computer-readable tangible storage devices 920, read via the respective R/W drive or interface 918, and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the sequential pattern mining program 110a in client computer 102 and the sequential pattern mining program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the sequential pattern mining program 110a in client computer 102 and the sequential pattern mining program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926, and computer mouse 928. The device drivers 930, R/W drive or interface 918, and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
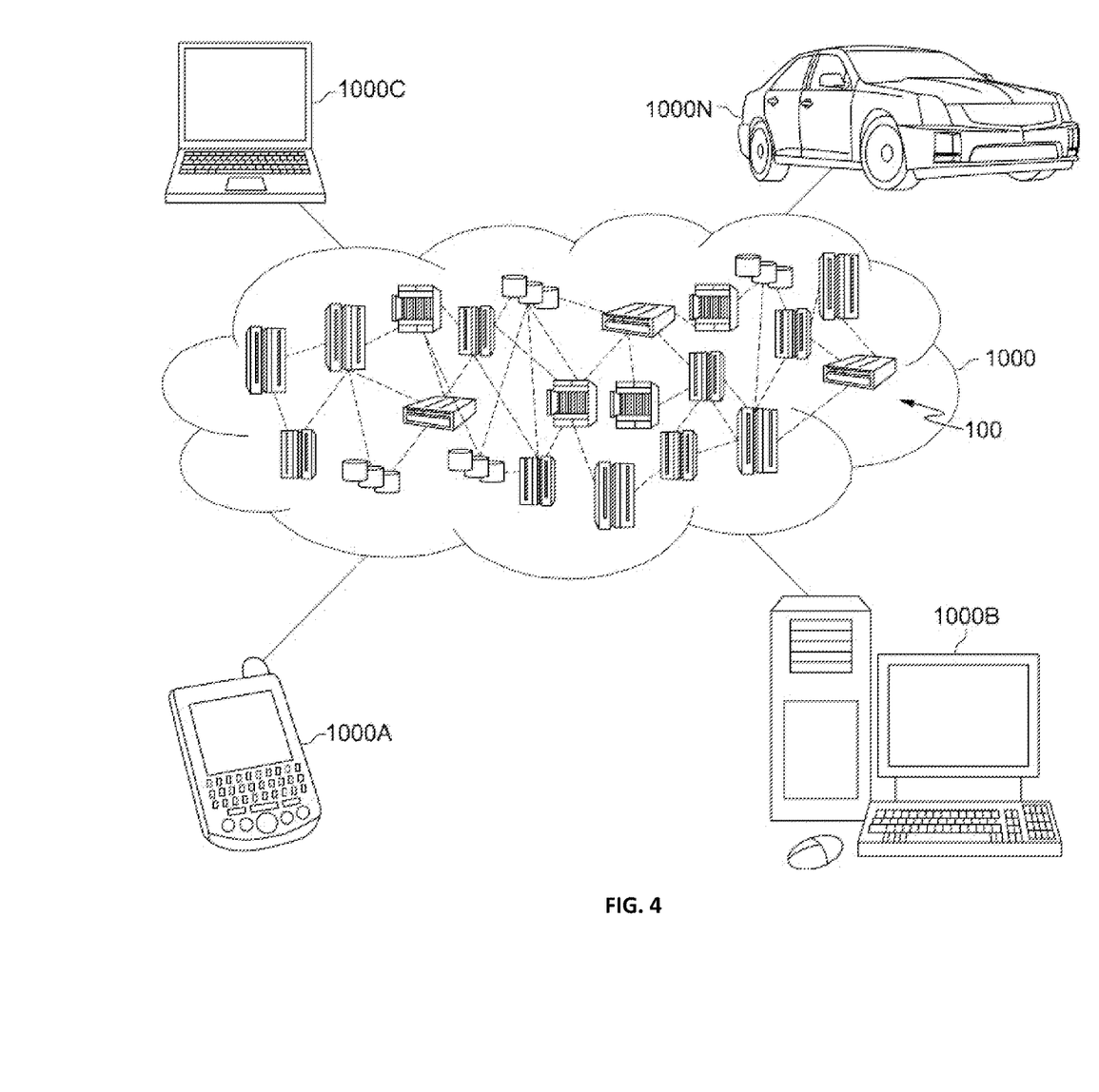
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
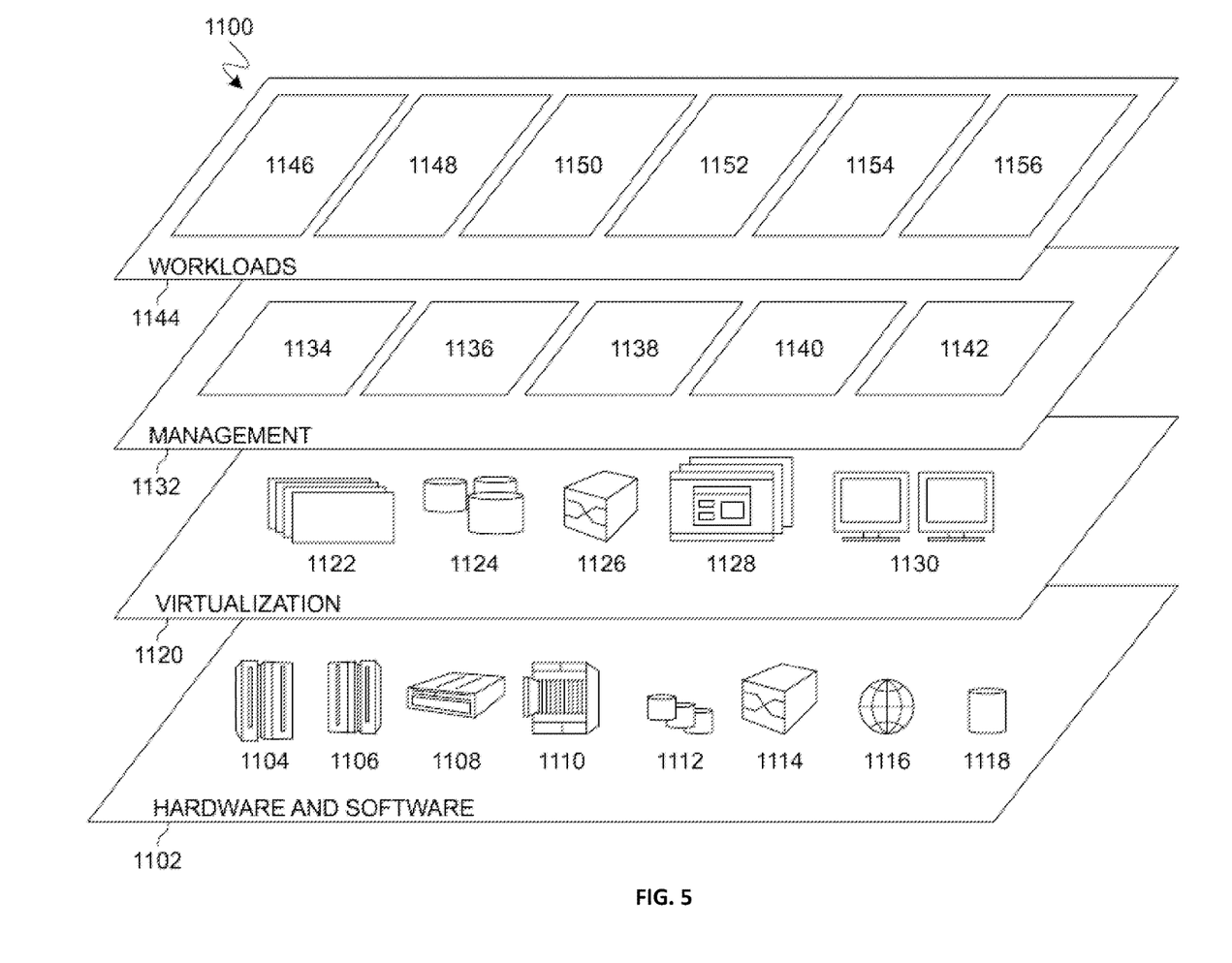
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and sequential pattern mining 1156. A sequential pattern mining program 110a, 110b provides a way to mine data using a relative inter-arrival time tolerance.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for sequential pattern mining, the method comprising:
   receiving a data mining parameter;
   computing a plurality of frequent sequences based on the received data mining parameter;
   extracting a subsequence with temporal annotations for each frequent sequence within the computed plurality of frequent sequences;
   clustering the subsequence based on a plurality of temporal intervals using a relative time window and a density based algorithm, wherein the relative time window of the clusters of the subsequence is based on verifying that a time difference between a first subsequence time stamp and a second subsequence time stamp is less than the time that the second subsequence time stamp happened multiplied by a relative time tolerance; and
   producing an output based on the clustered plurality of temporal intervals.

2. The method of claim 1, wherein the data mining parameter is entered by a user as a relative time window threshold and a minimum support value, wherein the minimum support value includes the number of times the subsequence matches within a dataset.

3. The method of claim 1, wherein the data mining parameter is a minimum support value.

4. The method of claim 3, further comprising:
   receiving a second parameter, wherein the second data mining parameter is a relative time window threshold.

5. The method of claim 1, wherein the data mining parameter is a relative time window threshold.

6. The method of claim 1, wherein the plurality of frequent sequences is computed without temporal annotations.

7. A computer system for sequential pattern mining, comprising:
   one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
   computing a plurality of frequent sequences based on the received data mining parameter;
   extracting a subsequence with temporal annotations for each frequent sequence within the computed plurality of frequent sequences;
   clustering the subsequence based on a plurality of temporal intervals using a relative time window and a density based algorithm, wherein the relative time window of the clusters of the subsequence is based on verifying that a time difference between a first subsequence time stamp and a second subsequence time stamp is less than the time that the second subsequence time stamp happened multiplied by a relative time tolerance; and
   producing an output based on the clustered plurality of temporal intervals.

8. The computer system of claim 7, wherein the data mining parameter is entered by a user as a relative time window threshold and a minimum support value, wherein the minimum support value includes the number of times the subsequence matches within a dataset.

9. The computer system of claim 7, wherein the data mining parameter is a minimum support value.

10. The computer system of claim 7, wherein the data mining parameter is a relative time window threshold.

11. The computer system of claim 9, further comprising:
    receiving a second parameter, wherein the second data mining parameter is a relative time window threshold.

12. The computer system of claim 7, wherein the plurality of frequent sequences is computed without temporal annotations.

13. A computer program product for sequential pattern mining, comprising:
    one or more computer-readable storage media and program instructions stored on at least one of the one or more tangible storage media, the program instructions executable by a processor to cause the processor to perform a method comprising:
    program instructions to receive a data mining parameter;
    program instructions to compute a plurality of frequent sequences based on the received data mining parameter;
    program instructions to extract a subsequence with temporal annotations for each frequent sequence within the computed plurality of frequent sequences;
    program instructions to cluster the subsequence based on a plurality of temporal intervals using a relative time window and a density based algorithm, wherein the relative time window of the clusters of the subsequence is based on verifying that a time difference between a first subsequence time stamp and a second subsequence time stamp is less than the time that the second subsequence time stamp happened multiplied by a relative time tolerance; and
    program instructions to produce an output based on the clustered plurality of temporal intervals.

14. The computer program product of claim 13, wherein the data mining parameter is entered by a user as a relative time window threshold and a minimum support value, wherein the minimum support value includes the number of times the subsequence matches within a dataset.

15. The computer program product of claim 13, wherein the data mining parameter is a minimum support value.

16. The computer program product of claim 15, further comprising:
program instructions to receive a second parameter, wherein the second data mining parameter is a relative time window threshold.

17. The computer program product of claim 13, wherein the data mining parameter is a relative time window threshold.

* * * * *